United States Patent
Van Werven-Franssen et al.

[11] Patent Number: 5,820,613
[45] Date of Patent: Oct. 13, 1998

[54] BALLOON CATHETER WITH REINFORCED AND ELASTICALLY DEFORMABLE BASIC BODY

[75] Inventors: Gerda Hendrika Maria Van Werven-Franssen, Roden; Rudolf Kornelis Lunsche, Peize; Lucas Joannes Hijlkema, Groningen, all of Netherlands

[73] Assignee: Cordis Corporation, Miami Lakes, Fla.

[21] Appl. No.: 594,998

[22] Filed: Jan. 31, 1996

[30] Foreign Application Priority Data

Jan. 31, 1995 [NL] Netherlands ................. 9500173

[51] Int. Cl.⁶ ..................................... A61M 25/00
[52] U.S. Cl. ..................... 604/282; 604/96; 604/280; 606/192
[58] Field of Search ................ 128/772, 657; 604/96, 103, 53, 282, 264, 280; 606/194, 192

[56] References Cited

U.S. PATENT DOCUMENTS

| | | | |
|---|---|---|---|
| 4,276,874 | 7/1981 | Wolvek et al. | 128/1 D |
| 4,351,341 | 9/1982 | Goldberg et al. | 128/348 |
| 4,715,378 | 12/1987 | Pope, Jr. et al. | 128/344 |
| 4,813,934 | 3/1989 | Engelson et al. | 604/99 |
| 4,838,268 | 6/1989 | Keith et al. | |
| 5,078,727 | 1/1992 | Hannam et al. | 606/194 |
| 5,125,895 | 6/1992 | Buchbinder et al. | 604/95 |
| 5,176,661 | 1/1993 | Evard et al. | 604/282 |
| 5,209,727 | 5/1993 | Radisch, Jr. et al. | |
| 5,250,069 | 10/1993 | Nobuyoshi et al. | 606/192 |
| 5,304,198 | 4/1994 | Samson | 606/194 |
| 5,338,295 | 8/1994 | Cornelius et al. | 604/96 |
| 5,338,299 | 8/1994 | Barlow | 604/96 |
| 5,460,608 | 10/1995 | Lodin et al. | 604/96 |
| 5,538,513 | 7/1996 | Okajima | 604/282 |

FOREIGN PATENT DOCUMENTS

| | | |
|---|---|---|
| 0388486 | 9/1990 | European Pat. Off. |
| 0408198 | 1/1991 | European Pat. Off. |

*Primary Examiner*—Corrine M. McDermott
*Assistant Examiner*—Cris L. Rodriguez
*Attorney, Agent, or Firm*—Thomas R. Vigil

[57] ABSTRACT

The balloon catheter comprises a tube-like basic body having a distal end-section in which a balloon member is arranged. The inside of the balloon member is connected, via a lumen in the basic body, with a connecting member at the proximal end of the basic body. Via this connecting member and the lumen, liquid or gas under pressure can be supplied to the balloon, in order to expand the latter. The distal end-section is stiff and elastically deformable.

14 Claims, 2 Drawing Sheets

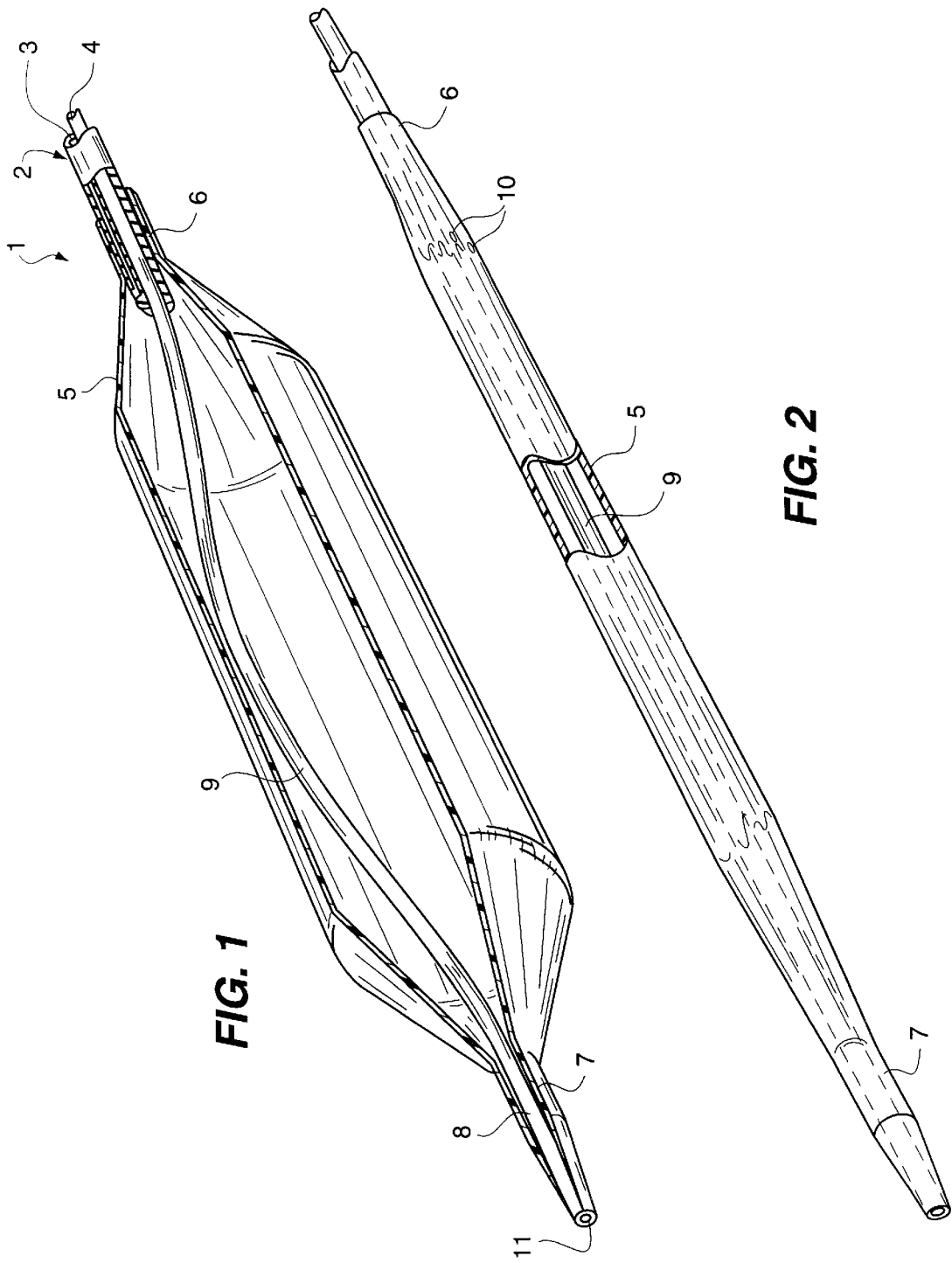

BALLOON CATHETER WITH REINFORCED AND ELASTICALLY DEFORMABLE BASIC BODY

BACKGROUND OF THE INVENTION

1. Field of the Invention

The present invention relates to a balloon catheter comprising a tube-like basic body having a balloon member arranged. The inside of the balloon member is connected, via a lumen in a distal end-section of the body. The inside of the balloon member is connected, via a lumen in the basic body, with a connecting member at the proximal end of the body. Via this connecting member and the lumen, liquid or gas under pressure can be introduced into the balloon, in order to expand the latter.

2. Description of the Related Art Including Information Disclosed Under 37 CFR §§ 1.97–1.99

Particularly in the case of balloon catheters with relatively large balloons, it is difficult to control the non-expanded balloon. Also in the non-expanded state, the balloon has a tendency to unfold, which can be troublesome when using the balloon. Returning to the non-expanded state following expansion, whereby the balloon should lie, preferably folded together, against the basic body, is difficult to achieve with large balloons.

Heretofore, analogous and non-analogous balloon catheters having a spring member in a balloon of the balloon catheter have been proposed. Several examples of such analogous and non-analogous balloon catheters are disclosed in the following U.S. Patents and EP Publication:

| U.S. Pat. No. | Patentee |
| --- | --- |
| 4,838,268 | Keith et al. |
| 5,078,727 | Carpenter et al. |
| 5,209,727 | Radisch et al. |
| EP Publication No. | Applicant |
| 0 388 486 | Gianfederico |

U.S. Pat. No. 5,078,727 discloses a balloon catheter comprising an outer body and an inner body which are connected to each other at their respective ends. When the balloon is inflated, the outer body is shortened relative to the inner body and the excess length of the inner body is taken up in the balloon by the inner body being bent into a coil. The balloon and outer body are made of layers of rigid and flexible polyurethane with an inner braided layer of polyester floss.

U.S. Pat. No. 5,209,727 discloses an elongate spring member positioned within an angioplasty balloon.

SUMMARY OF THE INVENTION

With the balloon catheter constructed according to the resent invention the above described drawbacks have been removed. The end-section of which the balloon has been arranged works, to a certain degree, as a spring which, on expansion of the balloon, is compressed axially and straightens the latter on reduction of the pressure inside the balloon.

The term "elastically deformable," used herein, means that the end section, following elastic deformation by the application of a force, returns more or less entirely to its original state. There will be no significant plastic deformation. The word "stiff" means a relatively high modulus of elasticity, so that a relatively considerable force is required to effect a certain deformation.

With expansion of the balloon member, the ends of the balloon move a little towards each other. This is particularly the case when the balloon has been made of a relatively inextensible material. As a result, both ends of the distal end-section will move towards each other as well, and consequently the distal end-section is stiff and elastically deformable, it continues to apply forces, working in opposite directions, on the ends of the balloon. As soon as the pressure on the balloon is reduced in order to release the expansion, the balloon is straightened immediately by the elastic action of the distal end-section.

An additional advantage of the balloon catheter constructed according to the teachings of the present invention is the fact that the catheter is more stable in blood vessels with a relatively strong flow. Consequently, the use of a so-called "long sheath" or a guiding catheter becomes superfluous.

In one suitable embodiment the basic body comprises an outer tube-like member and an inner tube-like member extends as far as the balloon member and the distal end-section comprises a section of the inner tube-like member. On expansion of the balloon, the inner tube-like member is compressed axially along its entire length, so that this entire inner tube-like member functions as an axial spring.

Also, preferably the balloon member is made of a relatively inextensible material and is pre-formed, and lies, in non-expanded state, in folds in the distal end-section.

The invention will be explained in greater detail in the following description with reference to the attached drawings.

BRIEF DESCRIPTION OF THE DRAWINGS

FIG. 1 is a perspective view of a distal end-section of a balloon catheter constructed according to the teachings of the present invention and shows a balloon thereof in expanded state and an inner tube-like element in a distorted, compressed state.

FIG. 2 is a perspective view of the distal end-section of the balloon catheter shown in FIG. 1 and shows the balloon in a non-expanded state and the inner tube-like element in a generally straight non-compressed state.

DESCRIPTION OF THE PREFERRED EMBODIMENT(S)

Figure 3:
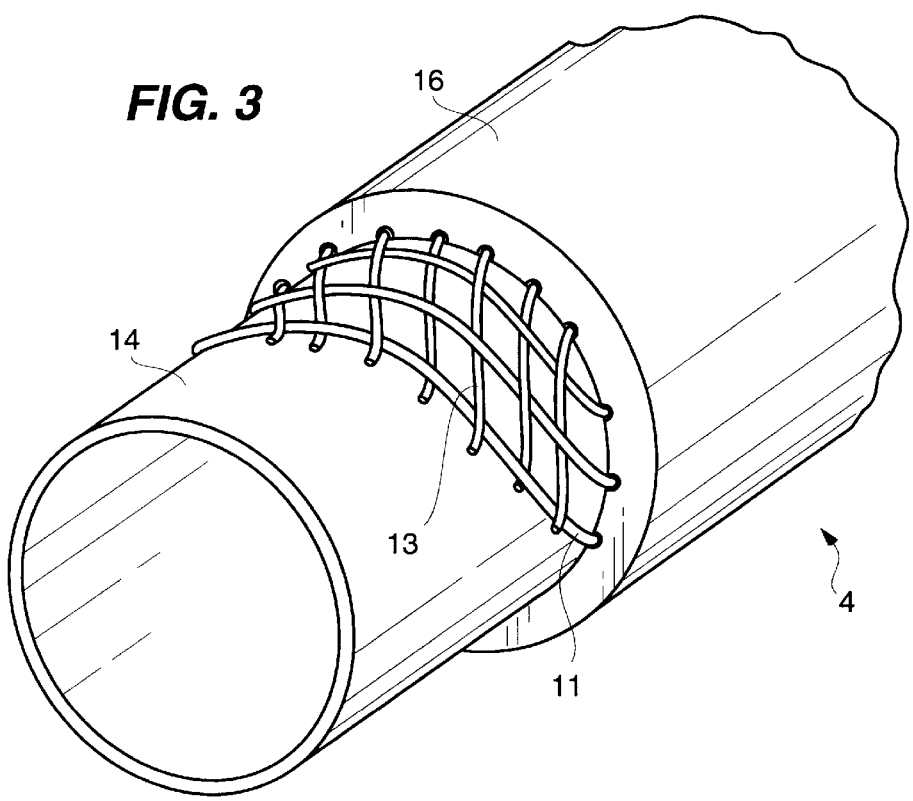
FIG. 3 is a fragmentary perspective view with portions broken away of one inner tube-like element constructed according to the teachings of the present invention.

FIG. 1 shows the working, distal end of a catheter 1. This catheter 1 comprises a tube-like basic body 2 in the usual manner.

In this embodiment, the tube-like basic body 2 comprises an outer tube-like element 3 and, received in a lumen thereof, is an inner tube-like element 4. The inner tube-like element 4 is itself also provided with a lumen which leads to the tip of the catheter on the left-hand side as shown in FIG. 1.

At the proximal end of the basic body 2 (not shown here), connecting members are provided which form connections with the lumens.

As shown in FIG. 1, the inner tube-like element 4 extends beyond the end of the outer tube-like element 3.

A balloon member 5 is arranged with one of its ends 6 connected to the end of the outer tube-like element 3 and with its other end 7 connected to the end 8 of the inner tube-like element 4.

The inside of the balloon member 5 is connected, via a channel 3a channel inside the lumen of the outer tube-like element 3, which has an annular cross-section, with a connecting element at the proximal end of the basic body 2. By supplying, via this channel 3a, a gas or liquid under pressure to the balloon member 5, the latter assumes the expanded state as illustrated in FIG. 1. In this expanded state the ends 6 and 7 of the balloon member 5 are situated closer together than is the case in the non-expanded state, as illustrated in FIG. 2. The end-section 9 of the basic body, which comprises in this embodiment only the inner tube-like element 4, has consequently been compressed, in the expanded state of the balloon member 5, in an axial direction so that this end-section 9 bends laterally or radially outwardly as shown in FIG. 1.

In a manner shown in FIG. 3, the inner tube-like element 4 is constructed in such a way that it comprises an embedded reinforcing layer of cross-braided wires 11 and 13 of stainless-steel wound around an inner tubular layer 14 and surrounded by an outer tubular layer 16. Consequently, this end-section 9 is stiff and elastically deformable. The end-section 9 forms, so to speak, a spring which has been put under tension as a consequence of the moving towards each other of the ends 6 and 7 of the balloon member 5 due to the expansion of the balloon member. Such reinforced catheter tubing is well known in the catheter art, going back to the Stevens U.S. Pat. No. 4,798,586.

As soon as the pressure in the balloon member 5 is relieved, the spring, formed by the end-section 9, will push the ends 6 and 7 of the balloon member 5 away from each other, as a result of which the balloon member 5 will lie itself in folds 10 against the end-section 9, as shown in FIG. 2. Consequently, the diameter of the balloon member 5 remains small which is favorable when introducing and withdrawing the catheter.

Figure 4:
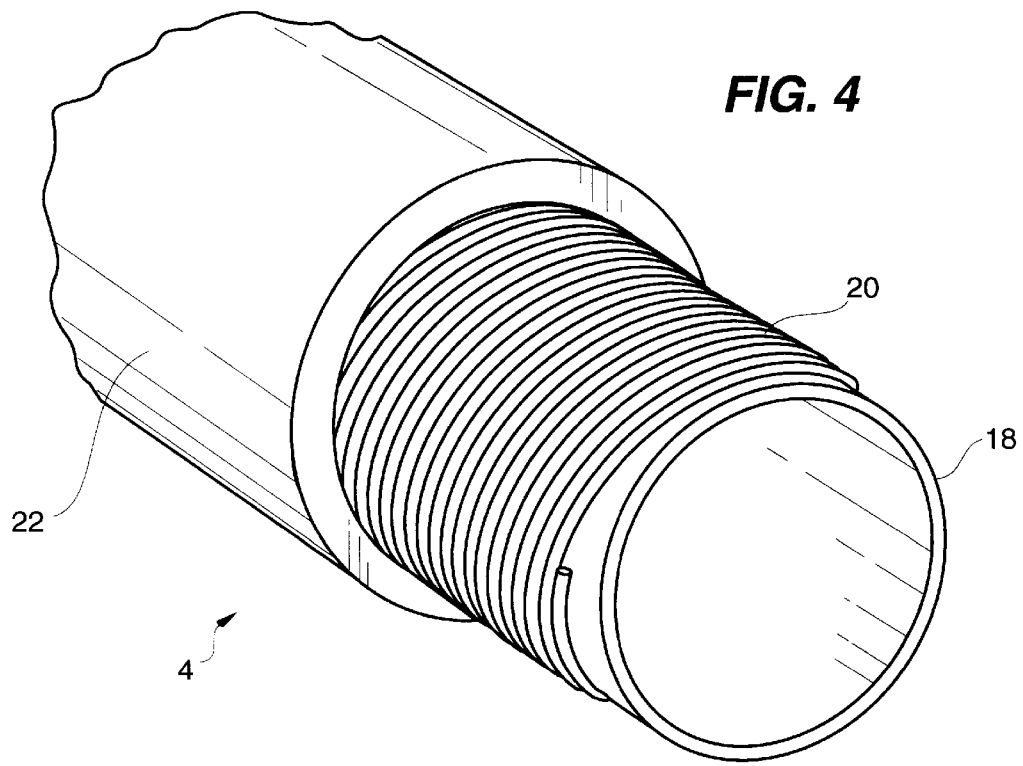
FIG. 4 is a fragmentary perspective view, with portions broken away, of another, inner tube-like element constructed according to the teachings of the present invention.

Another construction of the inner tube-like element 4 is shown in FIG. 4 and identified with reference numeral 4'. As shown, the inner tube-like element 4' includes an inner tubular layer 18, a coiled wire 20, which can be made of stainless steel and which can has coils positioned closely adjacent each other, as shown, and an outer tubular layer 22.

The balloon member 5 has been made of a relatively inextensible material and is pre-formed, so that the expanded form is assumed from a specified minimum over pressure and remains the same over a large range of pressures.

The end-section 9 of the basic body 2 is stiff, reinforced and elastically deformable, which means that it can function as a spring which will, following the undoing of an elastic deformation due to a force applied to it, adopt its original shape again. The stiffness of the end-section 9 is chosen in such a way that it is sufficiently large to straighten, following expansion, the balloon member 5 in combination with which it is to be employed into the state illustrated in FIG. 2.

From the foregoing description, it will be apparent that the balloon catheter 1 with stiff, elastically deformable basic body 2 of the present invention has a number of advantages, some of which have been described above and others of which are inherent in the invention. Also it will be understood that modifications can be made to the balloon catheter 1 with stiff, elastically deformable basic body 2 described above without departing from the teachings of the present invention. Accordingly, the scope of the invention is only to be limited as necessitated by the accompanying claims.

We claim:

1. A balloon catheter comprising a tube-like basic body having a proximal end, a distal end, a distal end section and at least one lumen extending through said basic body, said proximal end being adapted to be connected to a connecting member for communicating with said lumen and a balloon member arranged around said distal end-section, extending distally therefrom and which is longer in a deflated state than in an inflated state, an inner, second tube-like basic body extending through said one lumen of said tube-like basic body and through said balloon member and being stiff, reinforced with an embedded reinforcing layer of braided wires, elastically deformable so that said second tube-like body bends like a spring, and extendable when said balloon member is in a deflated state to control the profile of said balloon member.

2. The balloon catheter of claim 1 wherein said braided wires are made of stainless-steel.

3. The balloon catheter of claim 1 wherein said balloon member is made of a relatively inextensible material.

4. The balloon catheter of claim 1 wherein said balloon member is pre-formed, and lies, in a non-expanded state, in folds around said second tube-like basic body.

5. The balloon catheter of claim 1 wherein said balloon member has a proximal end which is fixed to said distal end of said first tube-like basic body and said second tube-like basic body extends through said distal end of said first tube-like basic body.

6. In a balloon catheter comprising a first tubular body having a proximal end, a distal end, and a distal end section and a second tubular body received in said first tubular body, the improvement residing in said second tubular body being stiff, reinforced with an embedded reinforcing layer of wires and elastically deformable so that said second tubular body bends like a spring, and comprising at least two generally tubular layers, an outer layer and an inner layer, and a balloon member which is made of relatively inextensible material, which is mounted to and around said second tubular body and which is longer in a deflated state than in an inflated state, and said second tubular body being extendable when said balloon member is in a deflated state to control the profile of said balloon member.

7. The balloon catheter of claim 6 wherein said second tubular body includes a third intermediate generally tubular layer located between said inner and outer tubular layers.

8. The balloon catheter of claim 7 wherein said third intermediate generally tubular layer is made of cross-braided wires wound around said inner tubular layer.

9. The balloon catheter of claim 7 wherein said third intermediate generally tubular layer is defined by a coiled wire coiled around said inner tubular layer.

10. The balloon catheter of claim 9 wherein the coils of said coiled wire are positioned closely adjacent each other around said inner tubular layer.

11. The balloon catheter of claim 6 wherein said balloon member is made of a relatively inextensible material.

12. The balloon catheter of claim 6 wherein said balloon member is pre-formed, and lies, in a non-expanded state, in folds around said second tubular body.

13. A balloon catheter comprising a first tube-like basic body having a proximal end, a distal end and a distal end-section and a second tube-like basic body received in said first tube-like basic body, a balloon member arranged around said second tube-like basic body, said balloon member being longer in a deflated state than in an inflated state, means in said first tube-like basic body for inflating said balloon member, said balloon member being adapted to be coupled to said means for inflating said balloon member and said second tube-like basic body being stiff and elastically deformable and including cross-braided wires woven into a generally tubular shape and being extendable when said balloon member is in a deflated state to control the profile of said balloon member.

14. The balloon catheter of claim 13 wherein said balloon member has a proximal end which is fixed to said distal end of said first tube-like basic body, said second tube-like basic body extends through said distal end of said first tube-like basic body and said balloon member is pre-formed, and lies, in a non-expanded state, in elongate folds around said second tube-like basic body.

* * * * *